United States Patent
Sloth et al.

(10) Patent No.: US 9,814,526 B2
(45) Date of Patent: Nov. 14, 2017

(54) INTERVENTIONAL DRAPE COMPRISING A PATIENT INTERVENTIONAL DRAPE AND A BARRIER DRAPE

(75) Inventors: Erik Sloth, Risskov (DK); Thomas Fichtner Bendtsen, Aarhus (DK); Lars Knudsen, Risskov (DK)

(73) Assignee: USABCD A/A, Aarhus (DK)

( * ) Notice: Subject to any disclaimer, the term of this patent is extended or adjusted under 35 U.S.C. 154(b) by 0 days.

(21) Appl. No.: 13/703,359

(22) PCT Filed: Jun. 10, 2011

(86) PCT No.: PCT/DK2011/050205
§ 371 (c)(1),
(2), (4) Date: Dec. 11, 2012

(87) PCT Pub. No.: WO2011/154010
PCT Pub. Date: Dec. 15, 2011

(65) Prior Publication Data
US 2013/0087156 A1    Apr. 11, 2013

Related U.S. Application Data

(60) Provisional application No. 61/397,535, filed on Jun. 11, 2010.

(30) Foreign Application Priority Data

Jun. 11, 2010   (EP) ..................................... 10165692

(51) Int. Cl.
| | |
|---|---|
| *A61B 19/08* | (2006.01) |
| *A61B 46/00* | (2016.01) |
| A61B 17/00 | (2006.01) |
| A61B 46/23 | (2016.01) |
| A61B 46/10 | (2016.01) |
| A61B 46/20 | (2016.01) |

(52) U.S. Cl.
CPC .............. *A61B 19/08* (2013.01); *A61B 46/00* (2016.02); *A61B 46/10* (2016.02); *A61B 46/23* (2016.02);
(Continued)

(58) Field of Classification Search
CPC ....... A61B 19/08; A61B 19/081; A61B 19/10; A61B 19/087; A61B 2019/086;
(Continued)

(56) References Cited

U.S. PATENT DOCUMENTS 3,800,790 A * 4/1974 Collins .................. A61B 19/08
128/854
3,910,268 A * 10/1975 Miller .................... A61B 46/00
128/854
(Continued)

FOREIGN PATENT DOCUMENTS

| CN | 101180004 A | 5/2008 |
|---|---|---|
| GB | 2362323 | 11/2001 |
| WO | 2007062454 | 6/2007 |

*Primary Examiner* — Victoria J Hicks
(74) *Attorney, Agent, or Firm* — James Creighton Wray; Meera P. Narasimhan (57) ABSTRACT

A patient interventional drape for covering a person has at least one fenestration. A barrier drape is attached to the patient interventional drape. The barrier drape has at least one sterile cover. The barrier drape is attached to the patient interventional drape next to the at least one fenestration, thereby providing a sterile procedure area at the fenestration and a non-sterile area at the other side of the barrier drape, whereby a non-sterile person can handle procedural devices such as an ultrasonic transducer in the non-sterile area and provide the procedural devices to a healthcare person in the sterile procedure area when needed without any risk of contaminating the sterile procedure area.

9 Claims, 8 Drawing Sheets

(52) U.S. Cl.
CPC ............... *A61B 2017/00924* (2013.01); *A61B 2046/205* (2016.02)

(58) Field of Classification Search
CPC ....... A61B 19/086; A61B 46/00; A61B 46/10; A61B 46/20; A61B 46/23; A61B 46/30; A61B 2046/205; A61B 2046/201; A61B 2046/234; A61B 2046/236; A61B 2017/00924; A61B 46/13; A61B 46/27; A61B 46/40; A61B 46/17
USPC .................................. 128/854, 853, 849, 856
See application file for complete search history.

(56) References Cited

U.S. PATENT DOCUMENTS

| | | | |
|---|---|---|---|
| 4,040,418 A * | 8/1977 | Collins | A61B 46/23 128/852 |
| 4,457,026 A | 7/1984 | Morris | |
| 5,640,975 A | 6/1997 | Diao | |
| 6,244,268 B1 * | 6/2001 | Annett et al. | 128/849 |
| 6,615,836 B1 * | 9/2003 | Griesbach et al. | 128/849 |
| 6,840,935 B2 * | 1/2005 | Lee | A61B 17/42 128/898 |
| 6,978,785 B2 | 12/2005 | Lin | |
| 7,299,803 B2 | 11/2007 | Kovac | |
| 7,717,117 B2 | 5/2010 | Duarte | |
| 7,958,894 B2 | 6/2011 | Katoh | |
| 2002/0078964 A1 | 6/2002 | Kovac | |
| 2005/0224081 A1 | 10/2005 | Lin | |
| 2006/0076024 A1 | 4/2006 | Duarte | |
| 2007/0235038 A1 | 10/2007 | Alinsod | |
| 2007/0267028 A1 * | 11/2007 | Junk | 128/849 |
| 2008/0047567 A1 | 2/2008 | Bonutti | |
| 2009/0241970 A1 * | 10/2009 | Katoh et al. | 128/853 |

* cited by examiner

INTERVENTIONAL DRAPE COMPRISING A PATIENT INTERVENTIONAL DRAPE AND A BARRIER DRAPE

This application claims the benefit of European Application No. 10165692.4 filed Jun. 11, 2010, U.S. Provisional Application Ser. No. 61/397,535 filed Jun. 11, 2010, and PCT/DK2011/050205 filed Jun. 10, 2011, International Publication No. WO 2011/154010, and the amended sheets from the IPRP, which are hereby incorporated by reference in their entirety as if fully set forth herein.

FIELD OF THE INVENTION

The present invention relates to an interventional drape, in particular for procedures involving devices for visualisation of the exact location of an interventional procedure such as an ultrasonic device.

BACKGROUND OF THE INVENTION

Interventional drapes including surgical drapes serve to keep the area of the interventional procedure site as clean and sterile as possible. Most of the drapes feature, for that purpose, apertures formed according to the procedure site, the so-called fenestrations, or these can be correspondingly cut before the beginning of the procedure.

After the skin of the patient has been cleaned and disinfected, the drape is arranged with regard to the procedure site i.e. arranging the fenestration around the procedure site. The exact location of interventional procedure sites is visualised two- or three-dimensionally before the procedure takes place by MRI, MRT, X-ray or ultrasound in order to localize the target as precisely as possible and hereby, also to protect the surrounding tissue as much as possible.

This is illustrated for example by the statement of the National Institute for Clinical Excellence (NICE) on the use of ultrasound locating devices for placing central venous catheters (Technology Appraisal Guidance No. 49, September 2002) by stating that "Two-dimensional imaging ultrasound guidance is recommended as the preferred method for insertion of central venous catheters into the internal jugular vein in adults and children in elective situations." A recently published study concludes that implementation of the NICE guidelines significantly reduces the number of complications observed during or after the insertion (Wigmore T J et al., Br J Anaesth. 2007 November; 99(5): 662-5).

The position of the exact procedure site can be marked and the device for visualisation removed before the procedure takes place. However, minor movements of the patient often change the location for the exact procedure site. Thus, in order not to loose the location of the procedure site before or during the procedure, real-time visualisation can be maintained during the entire procedure. Thus, the device for visualisation should be covered as sterile as possible in order to maintain a continuous visualisation of the target during the procedure.

In the field of ultrasonic guidance this has been solved by using a sterile cover for the ultrasonic transducer separate from the interventional drape as described in EP 1 104 618.

Additionally, US 2007/0267028 describes an interventional drape with a first fenestration and a fluid collection pouch where the interventional drape comprises at least one further fenestration for reception of a sterile cover for a means of reference e.g. infrared emitters and receivers protruding from the level of the surface of the drape whereby two- and three-dimensional visualisation systems can be used during the procedure. The means of reference are to be inserted from the side of the interventional drape facing the patient and are to be arranged before the procedure.

It is important due to the non-sterility of the device for visualisation that the cover is able to prevent any risk of contamination to the procedure site. Still, flexible movement is essential to obtain an exact visualisation of the anatomical target.

OBJECT OF THE INVENTION

It is the object of the present invention to provide an interventional drape which apart from enabling sterility at the interventional procedure site also provides a sterile cover for a procedural means and at the same time allows the procedural means to be used in a flexible manner.

DESCRIPTION OF THE INVENTION

The object of the invention can be fulfilled with an interventional drape comprising a patient interventional drape for covering a person and with a least one fenestration and a barrier drape attached to said patient interventional drape, where said barrier drape comprises at least one sterile cover where said barrier drape is attached next to said at least one fenestration, thereby providing a sterile procedure area of the patient interventional drape at the front side of the barrier drape facing said fenestration and a non-sterile area at the back side of said barrier drape, thereby forming a sterile space above the sterile procedural area and a non-sterile space above the non-sterile area, whereby a non-sterile person can handle a procedural means such as an ultrasonic transducer in said non-sterile space and provide said procedural means to a healthcare person in said sterile space when needed without any risk of contaminating said sterile procedure area.

The interventional drape of the present invention comprises a patient interventional drape, which is the part of the interventional drape that is to be in contact with the patient. The patient interventional drape further includes at least one fenestration to allow access to the procedure site. The patient interventional drape can be provided with one single fenestration or with more fenestrations for multiple procedure sites. Attached to the patient interventional drape is a barrier drape which is provided with at least one sterile cover for procedural means.

Throughout the description the term "sterile procedure area" is to be understood as the area of the patient interventional drape comprising the at least one fenestration and limited by the attachment of the barrier drape.

Throughout the description the term "healthcare person" is to be understood as any person performing the procedure, preferably professional staff such as paramedics, physicians, and nurses.

By "procedural means" are to be understood devices permitting two- or three-dimensional visualisations e.g. infrared, near-infrared or ultrasound. In addition, "procedural means" as well comprise other devices such as keyboards or computer units employed for typing commands or data during the procedure while maintaining the sterility of the healthcare person.

The barrier drape is kept sterile at its front side facing fenestration and the sterile procedure area and thus creates a sterile space arranged above the sterile procedure area and in front of the front side. Thus there is no requirement that the barrier drape is kept sterile on the back side of the barrier drape. Therefore, the back side of the barrier drape facing away from the sterile space in front of the barrier drape can be non-sterile and still provide a sterile procedure area and a sterile space arranged above the sterile procedure area due to the barrier effect of the barrier drape. Hereby, a part of the patient interventional drape may be non-sterile as well. Thus, even though a non-sterile area is provided at the side behind the barrier drape then the sterile procedure area is provided. This enables a person who is non-sterile to be placed at the side behind the barrier drape and provide procedural means such as a keyboard or an ultrasonic transducer to the healthcare person.

The barrier drape is attached to the patient interventional drape at a position next to a fenestration of the patient interventional drape. Additionally, it can be attached along one of the sides of the patients interventional drape or in a position therein between. The position of the attachment is dependent upon the purpose of the interventional drape. The attachment of the barrier drape provides a sterile space above the sterile procedure area at said fenestration at the front side of the barrier drape and a non-sterile space above the non-sterile area at the back side of the barrier drape.

Attaching a barrier drape to a patient interventional drape enables procedural means to be inserted behind the barrier drape i.e. on the side of the barrier drape not facing the sterile procedure area and hereby to be covered by or inserted into a sterile cover provided in the barrier drape. The procedural means can then be provided to a healthcare person in the sterile procedure area. Oftentimes, procedural means are provided with electrical wires. Such wires are kept away from the sterile procedure area by the barrier drape which forms a barrier between the non-sterile procedural means and the sterile procedure area.

In addition, the procedural means can be handled by a non-sterile person who is able to provide the procedural means-when needed to the healthcare person without any risk of contaminating the sterile procedure area, since a barrier is formed between the sterile procedure area and the procedural means. Thus, in this manner any auxiliary personnel need not to be sterile. Hence, a lot of work and manpower can be saved since the auxiliary personnel can perform other tasks during the procedure and still be able to help the healthcare person in a sufficient manner. Thus, in addition less sterile clothing is to be used, which is a further economical benefit.

The interventional drape of the present invention can be used for interventional procedures especially catheter and needle insertions for example for amniocentesis, collection of biopsies for example from placenta or tumours, peripheral nerve blocks, central and peripheral vascular access etc. Furthermore, the interventional drape can be used for surgical procedures.

In a further embodiment, instrument pockets can be arranged on either the barrier drape or the patient interventional drape for the healthcare person to place instruments.

In a still further advantageous embodiment, said barrier drape and said patient interventional drape is formed from a single piece of material.

The barrier drape and the patient interventional drape can be formed from one single piece of material. The shaping of the material during the manufacturing process is performed in a manner whereby the part of the interventional drape which is in contact with the patient, i.e. the patient interventional drape, is to remain in position even when the other part of the interventional drape, i.e. the barrier drape, is moved during the procedure. This can for example be obtained by introducing an additional seam along the connection between the barrier drape and the patient interventional drape.

In another embodiment, the patient interventional drape of the interventional drape can comprise additional features on the sterile side facing the patient, such as a thin rubber layer or an adhesive tape, whereby the patient interventional drape is more adhesive and stick to the skin of the patient and has a less tendency for sliding. It is implicitly to be understood that these features can be present when the patient interventional drape and the barrier drape are formed from separate pieces of material.

In still another embodiment, small loops can be provided on the margins of the patient interventional drape in order to be attached either to the patient or to equipment, such as an operating table whereupon the patient is arranged. Hereby, the movement of the patient interventional drape part of the interventional drape is decreased while the movement of the barrier drape part of the interventional drape is still possible.

In an advantageous embodiment, at least part of said sterile cover is penetrative for radiation such as ultrasound.

When the procedural means is an ultrasonic transducer, it is important that at least a part of the sterile cover provided in the barrier drape is penetrative for the radiation e.g. ultrasound. The penetrability need only be in a minor part of the sterile cover in order to allow the radiation of the procedural means to pass through the sterile cover.

However, the sterile cover can be penetrative in a larger or smaller area. In one embodiment, the entire barrier drape is at least one sterile cover, which is penetrative.

The part of the sterile cover being penetrative for ultrasound can be made of any ultrasonic transparent material for example plastic, rubber, paper or silicone. The thickness of the material can vary depending on the specific characteristics of the material In a further advantageous embodiment, said at least one sterile cover is part of said barrier drape.

In one embodiment, the sterile cover can be an integrated part of the barrier drape. It is hereby understood that the whole barrier drape can function as a sterile cover for the procedural means and possibly be penetrative for radiation. Alternatively, only sections of the barrier drape functions as a sterile cover and these can be made of a material different from the material of the barrier drape. The procedural means can be introduced behind the barrier drape and pushed against or inserted into the sterile cover to be applied within the sterile procedure area.

As an alternative embodiment, the sterile cover in the barrier drape can be used as a cover of a keyboard or the entire ultrasonic device including keyboard and screen enabling the healthcare person to type on the keyboard. The attachment of the barrier drape to the patient interventional drape decreases the risk of the barrier drape to slide from the keyboard and accidentally expose the person performing the procedure to a non-sterile surface.

Advantageously, at least a part of the barrier drape and/or at least a part of the sterile cover is composed from a rough material. Alternatively, material can be attached in order to make the surface rough to touch. The rough surface enables the healthcare person to easier move the procedural means along the procedure site and still obtain a strong visualisation.

In an advantageous embodiment, a clip can be attached to the procedural means such as an ultrasound transducer from the side of the barrier drape facing the sterile procedure area, in order to stabilize the procedural means behind the barrier drape.

In a further advantageous embodiment, a puncture device can be attached to the ultrasonic transducer on the side of the barrier drape facing the sterile procedure area. Hereby, the skin of the patient can easily be punctured after visualisation of the relevant tissue by the ultrasonic transducer.

In a still further advantageous embodiment, said at least one sterile cover is formed by one or more folds in said barrier drape.

The barrier drape can advantageously be folded with regard to the at least one sterile cover provided in the barrier drape. Folding of the sterile cover enables small pouches to be formed in the barrier drape. Within these pouches the procedural means can be arranged in the non-sterile space inside the pouches in a manner which enables the sterile cover to fit precisely to the procedural means e.g. in such way that ultrasonic transducer will be arranged precisely in relation to the part of the sterile cover provided in the barrier drape which is penetrative for the ultrasound. Thus the area provided for penetrability need only be a minor part of the sterile cover. Hereby the procedural means are kept in place in the pouches formed in the sterile cover and the procedural means can be operated by the healthcare person without the risk of inducing non-sterility.

In a further embodiment, the barrier drape can be folded and attached to the patient interventional drape to enclose the fenestration and provide a sterile space above the sterile procedure area, having an entrance opening where only the hands of the healthcare person has access in order to carry out the procedure.

Alternatively, the barrier drape is folded and attached to the patient interventional drape, leaving no access open and the procedure is carried out with the barrier drape between the sterile procedure area and the healthcare person.

In a still further advantageous embodiment, said at least one sterile cover is a pocket in said barrier drape.

Advantageously, the sterile cover has a form as a pocket which is provided in the barrier drape. The size and the shape of the pocket can be varied in order to be suitable for covering different types of procedural means. Furthermore, inserting a procedural mean in a pocket enables the healthcare person to easily grip the sterile cover with the procedural means and move this freely. Thus, the pocket increases the flexibility of the sterile cover.

The pocket can be of different shapes depending on the purpose of the pocket. In an advantageous embodiment, the pocket formed as a box can be used in order to cover a PDA, a remote control, a complete ultrasonic device, or a keyboard. Hereby, the healthcare person can type relevant data from the procedure directly into a computer unit or control the process of measuring during the procedure. Thus, auxiliary personnel are redundant since the process can be controlled by the healthcare person alone.

In a further advantageous embodiment, said pocket is detachable from said barrier drape.

Hereby, the pocket can be provided separately from the barrier drape and can be attached to the barrier drape before the procedure starts. This is an advantage during production where multiple different interventional drapes can be formed in a similar process by providing the barrier drape with one or more apertures.

Separate to the interventional drape, pockets of different shapes and sizes can be provided. Thus, the pocket for a specific procedure can be chosen and attached to a general barrier drape comprising one or more apertures. Hereby, high flexibility of the interventional drape is obtained.

In a still further advantageous embodiment, said pocket comprises a cylindrical shape.

In an advantageous embodiment the pocket is cylindrically shaped, which preferably resembles covers used for ultrasonic visualisation and known by a person skilled in the art. The length of the cylindrically shaped pocket can vary depending on the use of the interventional drape. If the interventional drape is to be used where ultrasonic visualisations are to be performed during the procedure and the ultrasonic device is to be arranged in a given position during the complete procedure, the cylindrically shaped pocket need only be of minor height. However, if the ultrasonic device is to be used actively during the procedure, the cylindrically shaped pocket needs to be longer in order to increase the mobility of the ultrasonic device.

A cylindrically shaped pocket can advantageously be combined with a pocket formed as a box in order to provide the healthcare person with more sterile equipment. For example, a cylindrically shaped pocket can be used for covering an ultrasonic transducer while the pocket formed as a box can be used in order to cover a remote control.

In a still further advantageous embodiment, said pocket comprises at least two finger-shaped protrusions.

Advantageously, the pocket can comprise two or more finger-shaped parts at least as part of the pocket in order to improve the catching ability of the healthcare person. In a first embodiment, the pocket can comprise two finger-shaped protrusions to obtain a grip like a pair of tweezers. In a second embodiment, the pocket can comprise five finger-shaped protrusions and function as a glove. Hereby, the healthcare person easier can grip for example an ultrasonic transducer with his non-sterile hands inserted into the pocket from behind the barrier drape.

In a still further advantageous embodiment, said barrier drape divides said fenestration of said patient interventional drape.

Thus, the barrier drape divides the fenestration into two separate parts—a first part on the side of the barrier drape facing the sterile procedure area and a second part on the side of the barrier drape facing away from the sterile procedure area i.e. behind the barrier drape. Since the side behind the barrier drape can be non-sterile it is important that the division of the fenestration separates the two parts efficiently. Thus, the first (sterile) part of the fenestration in the sterile procedure area is not contaminated by the second (non-sterile) part.

As an example, an ultrasonic transducer can be moved within the non-sterile part of the fenestration to visualise the tissue of interest and puncture of the skin can take place close to the barrier between the first and second part of the fenestration. Advantageously, the barrier between the first and second part of the fenestration is a sterile cover of the barrier drape, and visualisation can be performed here as well.

It is to be implicitly understood that the two parts of the fenestration need not be of equal size. Furthermore, it is to be understood that the barrier drape can be attached in a manner, where the part of the fenestration on the side of the barrier drape facing away from the sterile procedure area can be covered either with the barrier drape, a sterile cover in the barrier drape or a film penetrative for radiation.

In a still further advantageous embodiment, said barrier drape further comprises at least one partition means, said at least one partition means can be attached to said patient interventional drape to form a partition.

The area formed behind the barrier drape can be separated into more areas by attaching at least one partition means to the barrier drape as well as to the patient interventional drape. Hence, above the areas spaces can be formed, which can be used for different purposes for example one for keeping sterile non-used instruments, one for laying aside used instruments, and one for keeping non-sterile equipment such as ultrasonic transducers.

In a still further advantageous embodiment, the interventional drape further comprises at least one fixing means for securing wires; said fixing means are provided on said barrier drape and/or said patient interventional drape.

Advantageously, in order to prevent the wires from entering the sterile space above the sterile procedure area, a fixing means can be attached either to the patient interventional drape or the barrier drape whereby the wire is fixed. The fixing means can for example be a piece of adhesive tape or a clip, which either fixate the wire to a given length or allows the wire to slide at a fixed position with regard to the interventional drape. Hereby, the length of the wire can be continuously regulated. Additionally, this also prevents the procedural means from accidentally dropping from the interventional drape.

In a still further advantageous embodiment, said at least one sterile cover is attached to said barrier drape and/or said barrier drape is attached to said patient interventional drape by adhesive strips.

When the sterile cover is separate from the barrier drape and is attached before the procedure, the sterile cover can beneficially be attached to the barrier drape by adhesive strips, such as double-adhering tape as commonly known by the person skilled in the art or hook-and-loop fasteners.

Similarly, the attachment of the barrier drape to the patient interventional drape can be performed by the use of adhesive strips, such as double-adhering tape or hook-and-loop fasteners. Advantageously, the adhesive strips are sterile in order to maintain the sterility of the barrier drape and the patient interventional drape.

This invention further describes a kit which comprises an interventional drape as previously described, where said kit further comprises contact means. In an advantageous embodiment, said at least one contact means is an adhesive film penetrative for ultrasound.

Contact means are used during ultrasonic visualisations in order to increase the signal of e.g. ultrasound. The contact means is to be applied on the outside of the sterile cover of the barrier drape, i.e. between the sterile cover and the skin of the patient as well as on the inside of the sterile cover, i.e. between the ultrasonic device and the barrier drape.

Advantageously, the contact means is a gel or water. However, the contact means can be any substance which is capable of transmitting ultrasonic sound waves and displace air in order to enhance the visualisation such as an adhesive film. The adhesive film can be placed onto the sterile cover, the skin of the patient or onto the ultrasonic transducer. As an alternative the contact means can be an adhesive fluid containing pad, where the fluid can be a gel or water.

In a further embodiment, the adhesive film can be either an integrated part of the barrier drape or can be attached to the barrier drape, whereby the ultrasonic transducer can be adhered to the barrier drape.

Integrating the adhesive film as an integrated part of the barrier drape is advantageous if the adhesive film for example is arranged in a manner whereby the adhesive film easily is adhered in the fenestration when folding down the barrier drape. This means that the fenestration of the patient interventional drape is covered by an adhesive film present in the barrier drape. The adhesive film is penetrative to radiation and thus visualisation can be performed by an ultrasonic transducer before the barrier drape is pulled back and the skin punctured. It is implicitly to be understood that the barrier drape can be attached to the patient interventional drape either outside the fenestration or in a manner whereby the fenestration is divided.

In an advantageous embodiment, the kit for interventional procedures further comprises a separate drape to be arranged separately from said interventional drape.

Hereby, it is obtained that one kit provides sterile equipment for the procedure containing not only a sterile drape but also gel to be used and a drape to be placed separately onto a keyboard. The separate drape can be slightly adhesive on the side attached to the keyboard in order to stay on the surface of the keyboard and not to expose the healthcare person to a non-sterile surface.

In an alternative embodiment, the separate drape can be shaped as a pocket wherein a keyboard can be placed or folded whereby the separate drape can be placed on top of the keyboard. Hereby, the risk of exposure to non-sterility is decreased, since the separate drape is prevented from sliding off the keyboard accidentally.

With advantages the invention can be manufactured together with specific procedure kits for all the different procedures to which the invention applies. Those kits can e.g. contain individualised syringes, needles, gel, gloves, cleaning alcohol, ultrasound gel, additional covers and drapes, tubes, stabilising devices, pens, of different outline.

DETAILED DESCRIPTION OF THE INVENTION

Figure 1:
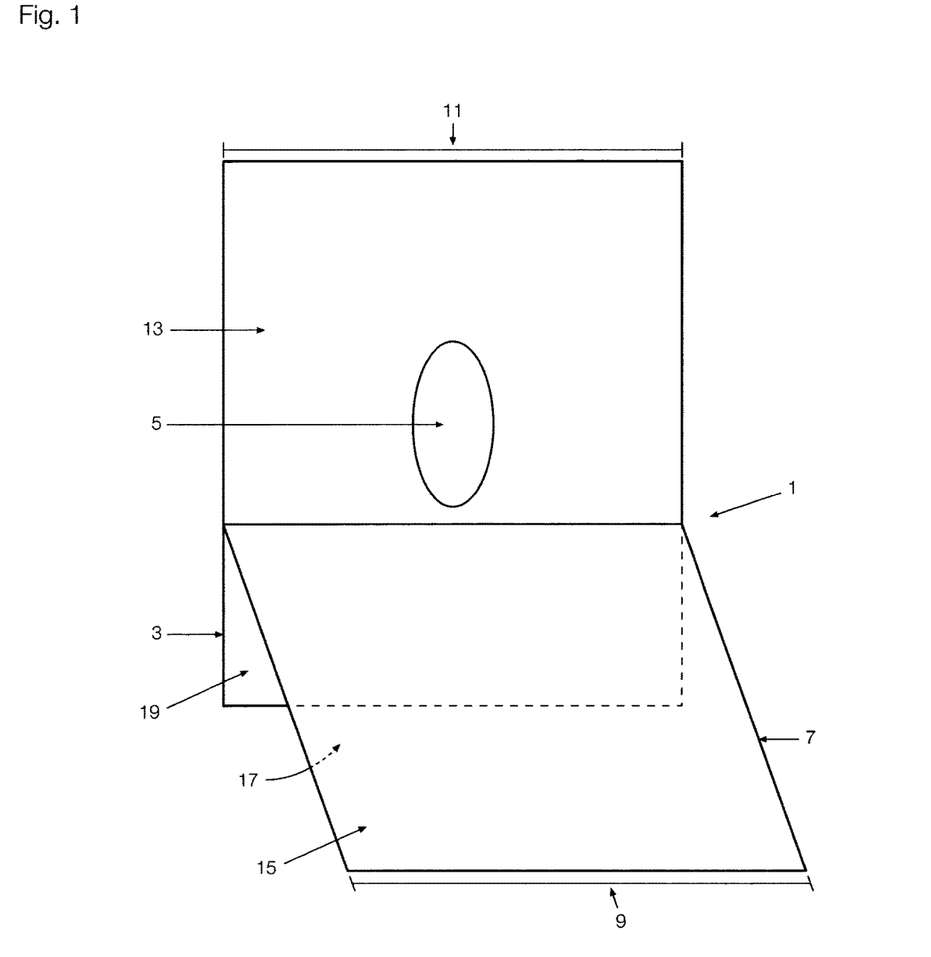
FIG. 1 illustrates an interventional drape comprising a patient interventional drape and a barrier drape attached to said patient interventional drape.

FIG. 1 illustrates an interventional drape 1 comprising a patient interventional drape 3 with one fenestration 5 and a barrier drape 7 attached to the patient interventional drape 3 next to the fenestration 5. In this embodiment, the width of the barrier drape 9 equals the width of the patient interventional drape 11. A sterile procedure area 13 is formed in front of the barrier drape 7 and is a sterile area where the procedure takes place through the fenestration 5. It is implicitly to be understood that the number of fenestrations are not to be limited to one per interventional drape but can be two, three or more depending on the procedure to be performed. Furthermore it is implicitly to be understood that the size and shape of the fenestrations are not to be limited by the ones illustrated in the figures but that the size and shape can be varied according to the procedure to be performed.

The barrier drape 7 is kept sterile at its front side 15 facing the sterile procedure area 13 and thus creates a sterile space arranged above the sterile procedure area 13 and in front of the front side 15. Thus there is no requirement that the barrier drape 7 is kept sterile on the back side 17 of the barrier drape 7. Therefore, the back side 17 of the barrier drape 7 facing away from the sterile procedure space in front of the barrier drape 7 can be non-sterile and still provide a sterile procedure area 13 and a sterile space arranged above the sterile procedure area 13 due to the barrier effect of the barrier drape 7. Hereby, a part 19 of the patient interventional drape 3 may be non-sterile as well. Thus, even though a non-sterile area is provided at the side behind the barrier drape 7 then the sterile procedure area 13 is provided. This enables a person who is non-sterile to be placed at the side 17 behind the barrier drape 7 and provide procedural means such as a keyboard or an ultrasonic transducer to the healthcare person.

Figure 2:
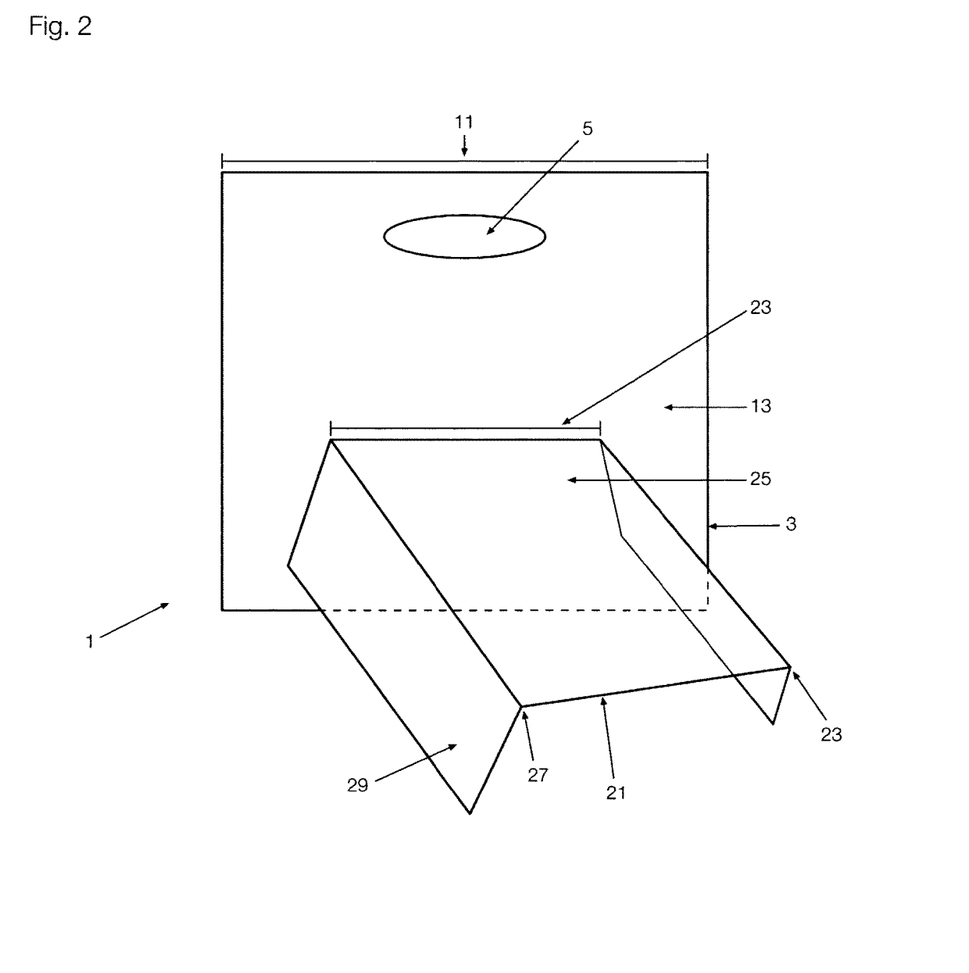
FIG. 2 illustrates an interventional drape where one sterile cover is formed by folds in the barrier drape.

FIG. 2 illustrates another embodiment of an interventional drape 1 comprising one fenestration 5 where a barrier drape 21 is attached to the patient interventional drape 3 in a more distant position than observed in FIG. 1. The width of the barrier drape 23 is less than the width of the patient interventional drape 11. However, the barrier drape 21 is folded in order to form a sterile cover 25 wherein the procedural means can easily be arranged. The folding 27 protects for example cables from sliding to the side 29, and the operating area 13 can be kept sterile even though the width of the barrier drape 23 is less than the width of the patient interventional drape 11.

Figure 3:
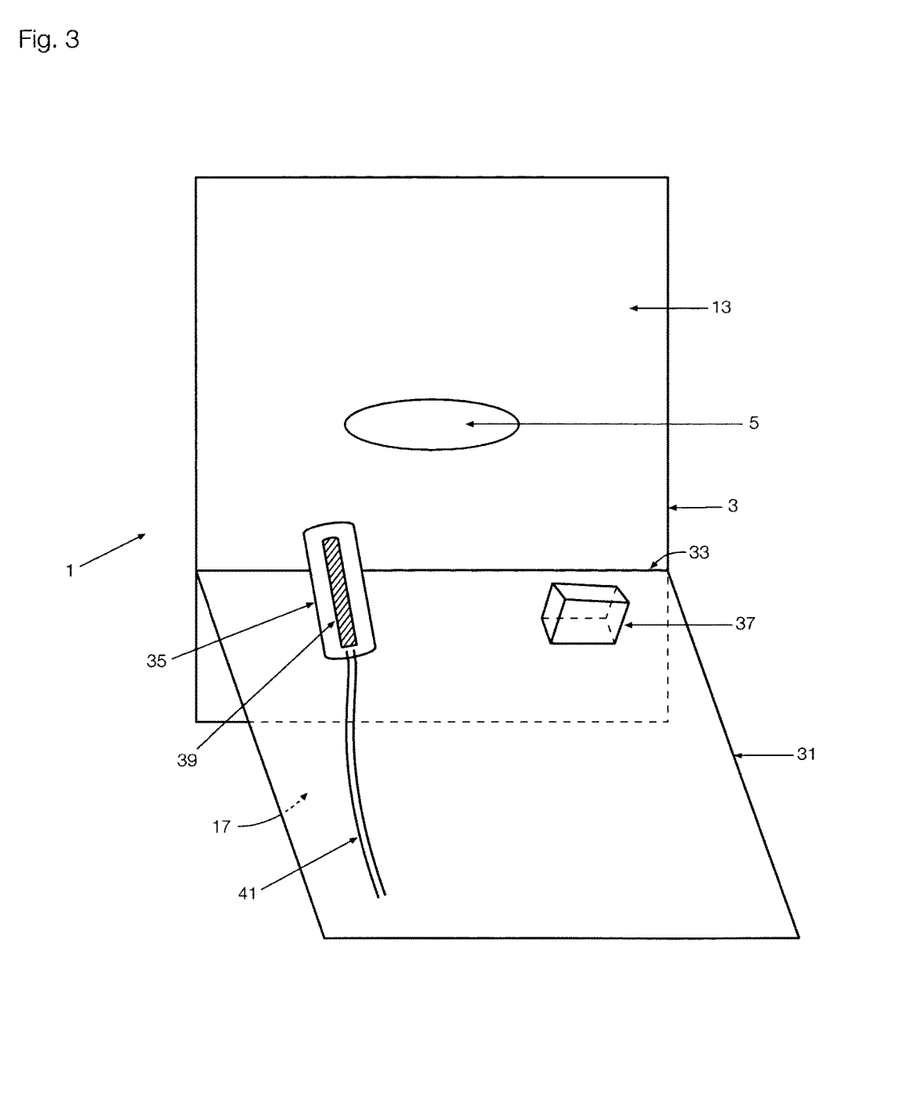
FIG. 3 illustrates an interventional drape comprising two sterile covers formed as pockets in the barrier drape.

FIG. 3 illustrates a further embodiment of an interventional drape 1 according to the invention. In this embodiment, the patient interventional drape 3 comprises one fenestration 5, and a barrier drape 31 is attached to the patient interventional drape 3 close to the fenestration 5. A sterile procedure area 13 is provided on the patient interventional drape 3 in the area with the fenestration 5 limited by the attachment 33 of the barrier drape 31.

In this particular embodiment, the barrier drape comprises two pockets 35, 37. One pocket is formed as a box 37 where into a keyboard and a PDA can be inserted. The other pocket is cylindrically shaped 35 and can comprise an ultrasonic transducer 39 as illustrated. The ultrasonic transducer 39 is inserted from the back side 17 of the barrier drape 31. Similarly, the keyboard or the PDA is inserted from this side. As illustrated, the cable 41 of the ultrasonic transducer 39 is kept on the back side 17 of the barrier drape 31 in the non-sterile area and does not interfere with the sterile procedure area 13.

At the beginning of a procedure, the patient is disinfected, and the interventional drape 1 arranged onto the patient by attaching the patient interventional drape 3 to the patient locating the fenestration 5 at the position of the procedure. Procedural means, such as an ultrasonic device 39 and a PDA, can be inserted into the pockets 35, 37 of the barrier drape 31.

The insertion of the procedural means 39 can be performed before the procedure starts, and thus the healthcare person can perform the insertion before the disinfection procedure is started ahead of the proper procedure. During the proper procedure, the healthcare person can handle the ultrasonic transducer 39 in the sterile cover 35 when needed in order to identify the exact position for the procedure. Thus, the healthcare person can advantageously perform the procedure alone.

Figure 4:
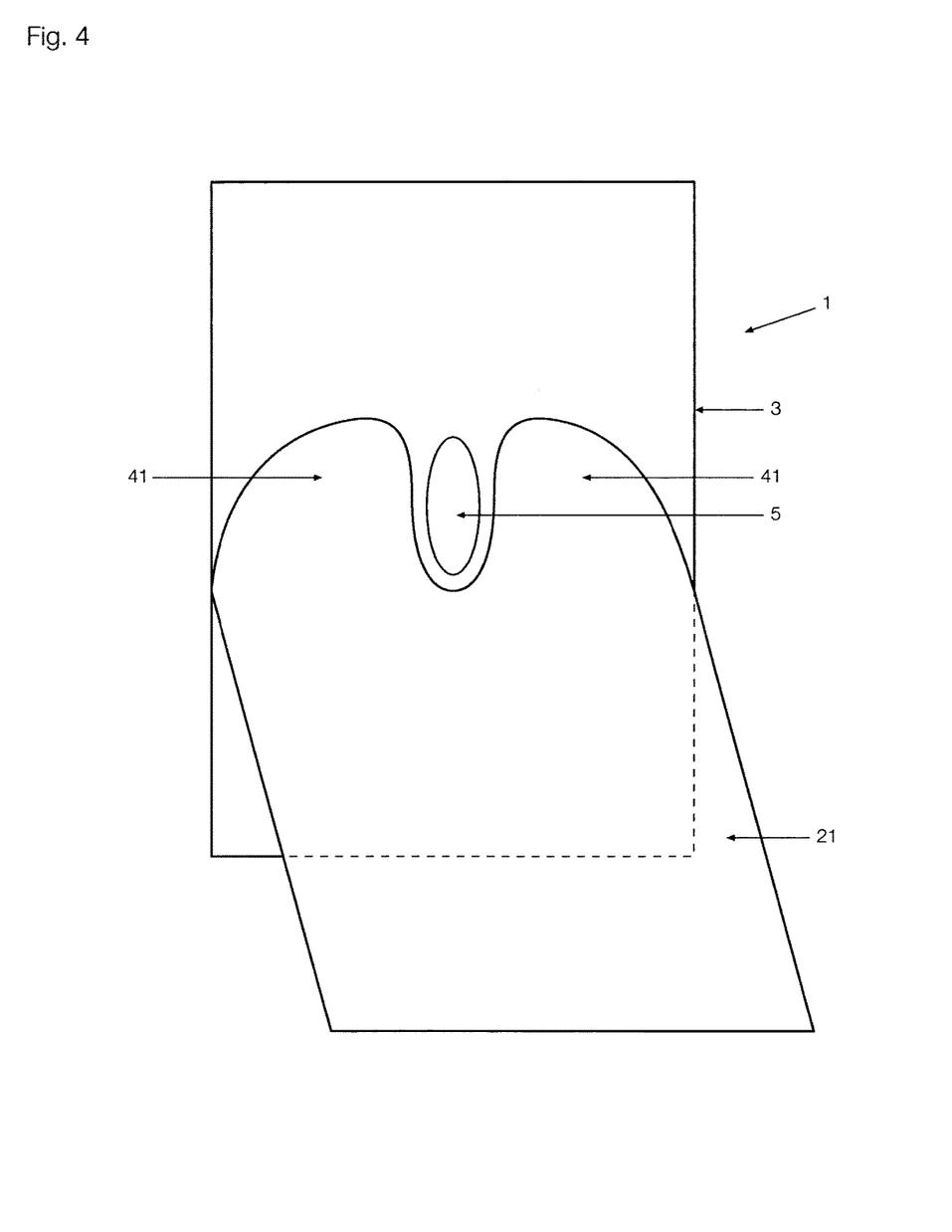
FIG. 4 illustrates an interventional drape where the barrier drape follows along the edges of the fenestration.

Alternatively, a non-sterile person can be situated at the back side 17 of the barrier drape 31. This person can be non-sterile since the person is not in contact with the sterile procedure area 13. However, the person is capable of providing one or more procedural means to the healthcare person, FIG. 4 illustrates a further embodiment of an interventional drape 1 comprising one fenestration 5 where a barrier drape 21 is folded and attached to the patient interventional drape 3 following close to the edge of the fenestration 5. The folding forms pouches 41 wherein a procedural means such as an ultrasonic transducer can be arranged. The size of the pouches 41 is large enough to ensure the flexibility when moving the transducer.

Figure 5:
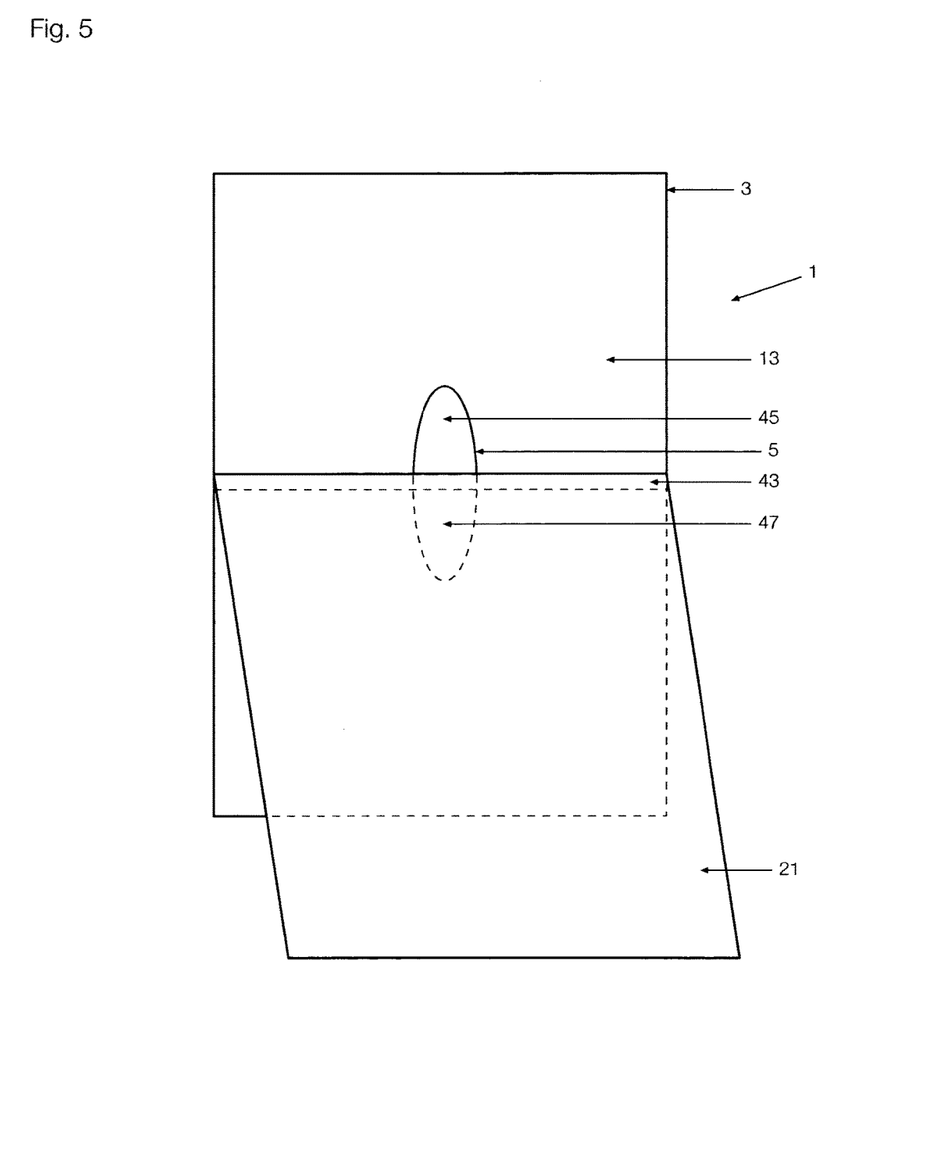
FIG. 5 illustrates an interventional drape where the barrier drape is arranged through the fenestration.

FIG. 5 illustrates a further embodiment of an interventional drape 1 comprising one fenestration 5 where a barrier drape 21 is attached to the patient interventional drape 3 by intersecting with the fenestration 5.

In this particular embodiment, the barrier drape 21 attaches to the patient interventional drape 3 with a band 43 that also attaches to the skin of the patient whereby the fenestration is divided into a first part 45 and a second part 47. The band 43 is capable of sealing off the first part 45 from the second part 47, whereby the first part 45 in the sterile procedure area 13 can be maintained sterile though the second part is non-sterile. The ultrasonic transducer can visualise for example a vein in the second part 47, and the puncture of the vein can be performed in the first part 45 of the fenestration 5 close to the band 43.

Figure 6:
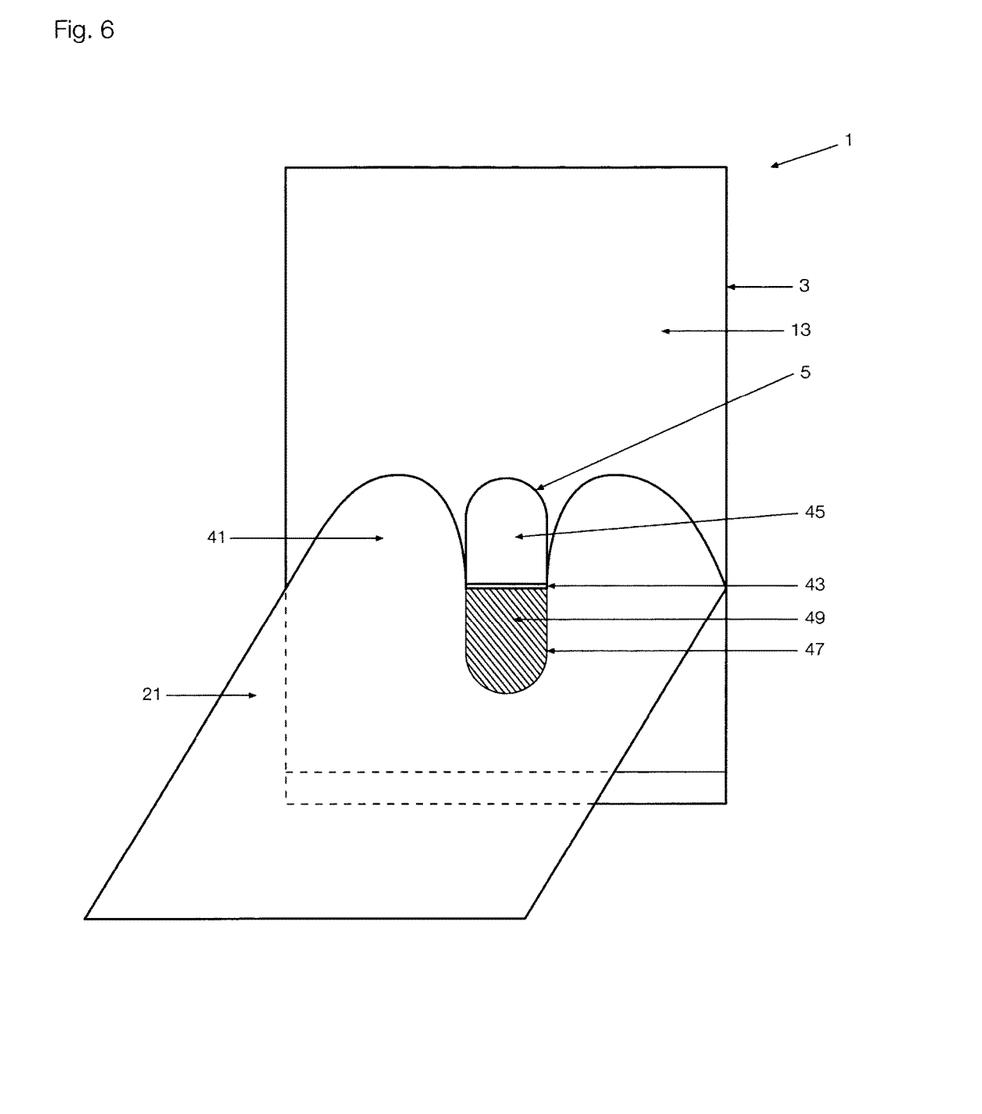
FIG. 6 illustrates an interventional drape where the barrier drape is arranged through the fenestration and follows along the edges of the fenestration.

FIG. 6 illustrates an alternative embodiment of the embodiment illustrated in FIG. 5. An interventional drape 1 comprising one fenestration 5 and a barrier drape 21 attached to the patient interventional drape 3 by intersecting with the fenestration 5 is illustrated. The barrier drape 21 is folded and attached to the patient interventional drape 3 in such way that edge parts of the barrier drape are arranged to be following close to the edge parts of the fenestration 5. The folding forms pouches 41, wherein the procedural means such as an ultrasonic transducer can be arranged. The size of the pouches 41 is large enough to ensure the flexibility when moving the transducer.

The barrier drape 21 attaches to the patient interventional drape 3 with a band 43 that also attaches to the skin of the patient whereby the fenestration is divided into a first part 45 and a second part 47. On the second part 47 of the fenestration 5 an adhesive film penetrative to ultrasound 49 is arranged. Advantageously, the ultrasonic transmitting film 49 is an integrated part of the interventional drape 1. However, the ultrasonic transmitting film 49 can as well be separately attached. In this manner, the ultrasonic transducer can visualise along the second part 47 of the fenestration and still be moved by the healthcare person situated at the front side of the barrier drape 21. In addition, the ultrasonic transducer can be used in the first part 45 of the fenestration 5 due to the pouches 41 of the barrier drape 21.

Figure 7:
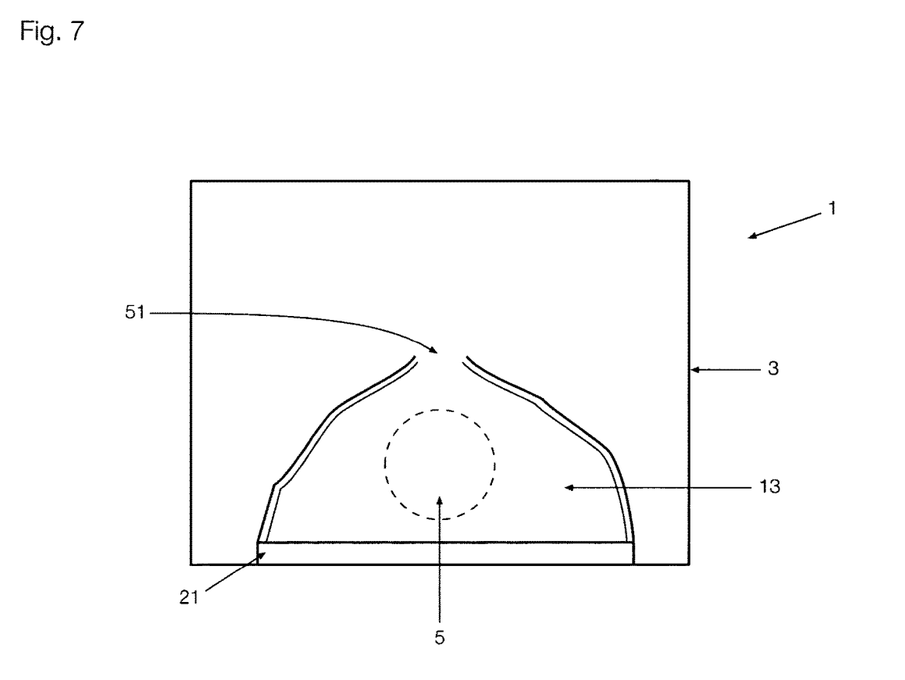
FIG. 7 illustrates an interventional drape where the barrier drape folds to form a sterile closure.

FIG. 7 illustrates a further embodiment of an interventional drape 1 comprising one fenestration 5 where a barrier drape 21 is attached to the patient interventional drape 3 and folded to enclose the fenestration. An opening 51 enables one or two sterile hands to enter the sterile procedure area 13 enclosed by the barrier drape 21. In this embodiment, only the hands performing the procedure need to be sterile. As an example, a sterile syringe can be arranged beside the fenestration 5 at the sterile procedure area 13. The healthcare person operates the syringe with one hand, while the other hand visualises the vein to be punctured handling an ultrasonic transducer arranged outside the sterile procedure area 13.

Figure 8:
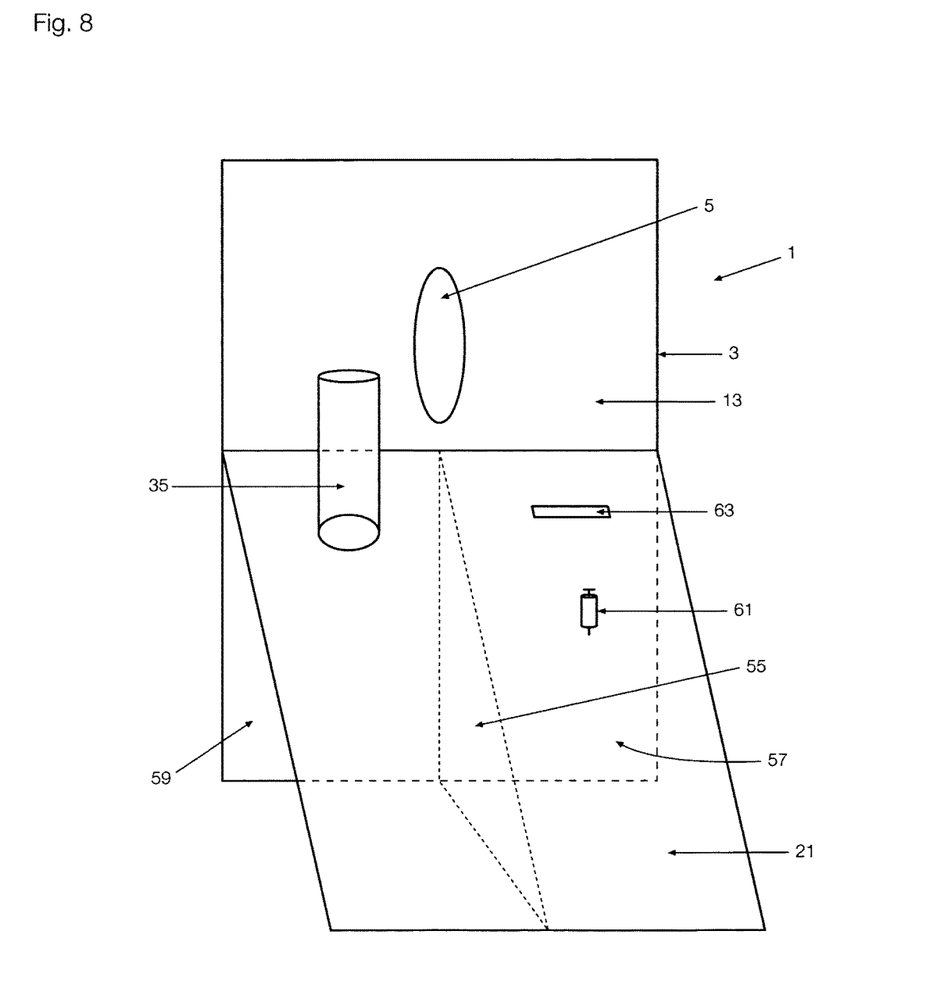
FIG. 8 illustrates an interventional drape where the barrier drape comprises a partition.

FIG. 8 illustrates a further embodiment of an interventional drape 1 comprising one fenestration 5 where a barrier drape 21 is attached to the patient interventional drape 3 and comprising a cylindrically shaped pocket 35. Furthermore, the barrier drape 21 comprises a slit 63 and one partition means 55. The partition means 55 is attached to the barrier drape 21 and the patient interventional drape 3. This forms two areas 57, 59 behind the barrier drape 21.

The two areas 57, 59 can thus be divided into for example a sterile 57 and a non-sterile 59 area. In the non-sterile space above the area 59 an ultrasonic transducer can be inserted into the cylindrically shaped pocket 35, while instruments can be arranged in the space above the sterile area 57 such as a syringe 61. The instruments can be accessed through a slit 63 of the barrier drape 21. After placing the equipment such as the ultrasonic transducer and a syringe 61 the barrier drape 21 can be arranged on the patient interventional drape 3 and advantageously, the attachment of the partition means to the barrier drape is arranged onto the attachment of the partition means to the patient interventional drape.

The invention claimed is:

1. An interventional drape comprising a patient interventional drape for covering a patient and with at least one fenestration and a barrier drape attached to said patient interventional drape, the interventional drape having a lower side for facing the patient and an upper side for facing away from the patient, where said barrier drape comprises at least one sterile cover wherein said barrier drape is attached next to said at least one fenestration, thereby providing a sterile procedural area of the patient interventional drape at a front side of the barrier drape facing said at least one fenestration and a non-sterile area at a back side of said barrier drape, thereby forming a sterile space above the sterile procedural area and above the upper side of the patient interventional drape at the front side of the barrier drape and a non-sterile space above the non-sterile area, and above the upper side of the patient interventional drape at the back side of the barrier drape, whereby a non-sterile person can handle a procedural means such as an ultrasonic transducer in said non-sterile space and provide said procedural means to a healthcare person in said sterile space when needed without any risk of contaminating said sterile procedure area; and wherein said at least one fenestration comprises an area and wherein said barrier drape is secured to the upper side of said patient interventional drape on opposite sides of said at least one fenestration only along an axis extending through and across said at least one fenestration so that the barrier drape divides said area of said at least one fenestration of said patient interventional drape into a sterile first part for interventional or surgical procedure in the sterile procedure area on a predetermined body part of the patient through the sterile first part of the at least one fenestration and a non-sterile second part by extending directly through and across said at least one fenestration.

2. The interventional drape according to claim 1, wherein at least part of said at least one sterile cover is penetrative for ultrasound radiation.

3. The interventional drape according to claim 1, wherein said at least one sterile cover is integrated in said barrier drape.

4. The interventional drape according to claim 1, wherein said interventional drape further comprises at least one fixing means for securing wires; said at least one fixing means is provided on said barrier drape and/or said patient interventional drape.

5. The interventional drape according to claim 1, wherein said at least one sterile cover is attached to said barrier drape and/or said barrier drape is attached to said patient interventional drape by adhesive strips.

6. A kit for interventional procedures comprising an interventional drape for covering a patient and with at least one fenestration and a barrier drape attached to said patient interventional drape, the interventional drape having a lower side for facing the patient and an upper side for facing away from the patient, where said barrier drape comprises at least one sterile cover wherein said barrier drape is attached next to said at least one fenestration, thereby providing a sterile procedural area of the patient interventional drape at a front side of the barrier drape facing said at least one fenestration and a non-sterile area at a back side of said barrier drape, thereby forming a sterile space above the sterile procedural area and above the upper side of the patient interventional drape at the front side of the barrier drape and a non-sterile space above the non-sterile area and above the upper side of the patient interventional drape at the back side of the barrier drape, whereby a non-sterile person can handle a procedural means such as an ultrasonic transducer in said non-sterile space and provide said procedural means to a healthcare person in said sterile space when needed without any risk of contaminating said sterile procedure area and wherein said barrier drape is secured to the upper side of said patient interventional drape on opposite sides of said at least one fenestration only along an axis extending through and across said at least one fenestration so that the barrier drape divides said at least one fenestration of said patient interventional drape into a sterile first part for interventional or surgical procedure in the sterile procedure area on a predetermined body part of the patient through the sterile first part of the at least one fenestration and a non-sterile second part by extending directly through and across said at least one fenestration, wherein said kit further comprises at least one contact means.

7. The kit for interventional procedures according to claim 6, wherein said at least one contact means is an adhesive film.

8. The kit for interventional procedures according to claim 7, wherein said adhesive film is an ultrasound transmitting film.

9. The kit for interventional procedures according to claim 6, wherein said kit further comprises a separate drape to be arranged separately from said interventional drape.

* * * * *

UNITED STATES PATENT AND TRADEMARK OFFICE
CERTIFICATE OF CORRECTION

PATENT NO. : 9,814,526 B2
APPLICATION NO. : 13/703359
DATED : November 14, 2017
INVENTOR(S) : Erik Sloth, Thomas Fichtner Bendtsen and Lars Knudsen It is certified that error appears in the above-identified patent and that said Letters Patent is hereby corrected as shown below:

On the Title Page

Item (73) Assignee, should read:
--USABCD A/S--

Signed and Sealed this
Twentieth Day of February, 2018

Andrei Iancu
*Director of the United States Patent and Trademark Office*